United States Patent
Viglione

(10) Patent No.: US 12,239,438 B2
(45) Date of Patent: Mar. 4, 2025

(54) BLOOD ANALYSIS DEVICES, SYSTEMS AND METHODS

(71) Applicant: QUANTUM INNOVATION AUSTRALIA PTY LTD, Parramatta (AU)

(72) Inventor: Dean Peter Viglione, Wentworth Point (AU)

(73) Assignee: QUANTUM INNOVATION AUSTRALIA PTY LTD, Parramatta (AU)

( * ) Notice: Subject to any disclaimer, the term of this patent is extended or adjusted under 35 U.S.C. 154(b) by 255 days.

(21) Appl. No.: 17/610,732

(22) PCT Filed: May 12, 2020

(86) PCT No.: PCT/AU2020/050465
§ 371 (c)(1),
(2) Date: Nov. 12, 2021

(87) PCT Pub. No.: WO2020/227756
PCT Pub. Date: Nov. 19, 2020

(65) Prior Publication Data
US 2022/0265169 A1    Aug. 25, 2022

(30) Foreign Application Priority Data

May 12, 2019    (AU) ................. 2019901615

(51) Int. Cl.
*A61B 5/145*    (2006.01)
*A61B 5/00*    (2006.01)
(Continued)

(52) U.S. Cl.
CPC ............ *A61B 5/145* (2013.01); *A61B 5/0035* (2013.01); *A61B 5/0075* (2013.01); *A61B 8/04* (2013.01);
(Continued)

(58) Field of Classification Search
CPC ..... A61B 5/145; A61B 5/0035; A61B 5/0075; A61B 8/04; A61B 8/4494; A61B 5/14532;
(Continued)

(56) References Cited

U.S. PATENT DOCUMENTS 4,565,017 A * 1/1986 Ottieri .................... A43C 11/16
36/118.1
5,109,849 A * 5/1992 Goodman ............ A61B 5/6834
600/513
(Continued)

FOREIGN PATENT DOCUMENTS

| WO | 2013/118115 A1 | 8/2013 |
| WO | 2013/165887 A1 | 11/2013 |
| WO | 2017/201093 A1 | 11/2017 |

OTHER PUBLICATIONS

International Written Opinion mailed Aug. 17, 2020, issued in PCT Patent Application No. PCT/AU2020/050465, 8 pages.

*Primary Examiner* — Tarifur R Chowdhury
*Assistant Examiner* — Akbar H. Rizvi
(74) *Attorney, Agent, or Firm* — Bauer and Joseph

(57) ABSTRACT

Methods and apparatus are provided for non-invasive blood analysis. A blood analysis device (10, 30) comprises a housing (24) for receiving a human or animal body part or a container of blood. The housing (24, 32) comprises at least one wave emitter (18) for emitting an emitted wave to target blood, and at least one wave sensor (26) for sensing a response wave after the emitted wave has interacted with the target blood. The at least one wave sensor is configured to output at least one sense signal allowing a frequency spectrum of the response wave to be constructed.

13 Claims, 8 Drawing Sheets

(51) Int. Cl.
  *A61B 8/00* (2006.01)
  *A61B 8/04* (2006.01)
  *G01N 24/08* (2006.01)
  *G01N 29/036* (2006.01)
  *G01N 29/06* (2006.01)
  *G01N 29/34* (2006.01)
  *G01N 29/46* (2006.01)

(52) U.S. Cl.
  CPC ........... *A61B 8/4494* (2013.01); *G01N 24/08* (2013.01); *G01N 29/036* (2013.01); *G01N 29/0654* (2013.01); *G01N 29/348* (2013.01); *G01N 29/46* (2013.01); *A61B 5/14532* (2013.01); *A61B 5/14546* (2013.01); *A61B 5/6802* (2013.01); *G01N 2291/02466* (2013.01); *G01N 2291/02809* (2013.01)

(58) Field of Classification Search
  CPC ..... A61B 5/14546; A61B 5/6802; A61B 8/02; A61B 8/0891; A61B 5/14535; A61B 5/14542; A61B 5/6824; A61B 5/1455; A61B 8/4227; A61B 8/4416; A61B 8/4477; A61B 8/5223; A61B 5/05; A61B 5/004; A61B 8/00; A61B 5/0013; A61B 5/0022; A61B 5/7235; A61B 5/742; A61B 8/06; A61B 2562/0204; A61B 2562/0223; A61B 2576/02; G01N 24/08; G01N 29/036; G01N 29/0654; G01N 29/348; G01N 29/46; G01N 2291/02466; G01N 2291/02809; G01N 2021/1765; G01N 21/31; G01N 29/42; G01N 29/4436; G01N 33/492; G01N 2021/3181; G01R 33/302; G01R 33/48

See application file for complete search history.

(56) References Cited

U.S. PATENT DOCUMENTS

| | | |
|---|---|---|
| 10,194,808 B1 | 2/2019 | Thompson et al. |
| 2008/0025872 A1* | 1/2008 | Dykes .............. A61B 5/150229 422/68.1 |
| 2012/0143247 A1* | 6/2012 | Smith ................ A61B 17/0643 606/220 |
| 2013/0144140 A1 | 6/2013 | Frederick et al. |
| 2015/0119661 A1* | 4/2015 | Gilbert ................ G01N 21/314 600/316 |
| 2015/0382105 A1* | 12/2015 | Thompson ........... A61B 5/6801 381/94.1 |
| 2017/0035308 A1 | 2/2017 | Gulati et al. |
| 2017/0156646 A1* | 6/2017 | Gulati .................. A61B 5/7203 |
| 2017/0234838 A1* | 8/2017 | Ten Grotenhuis ........................... G01N 29/0654 702/56 |
| 2017/0315111 A1* | 11/2017 | Wood ................ G01N 21/3577 |
| 2017/0354358 A1* | 12/2017 | Rajab ..................... G06F 3/147 |
| 2018/0028100 A1 | 2/2018 | Martius et al. |

\* cited by examiner

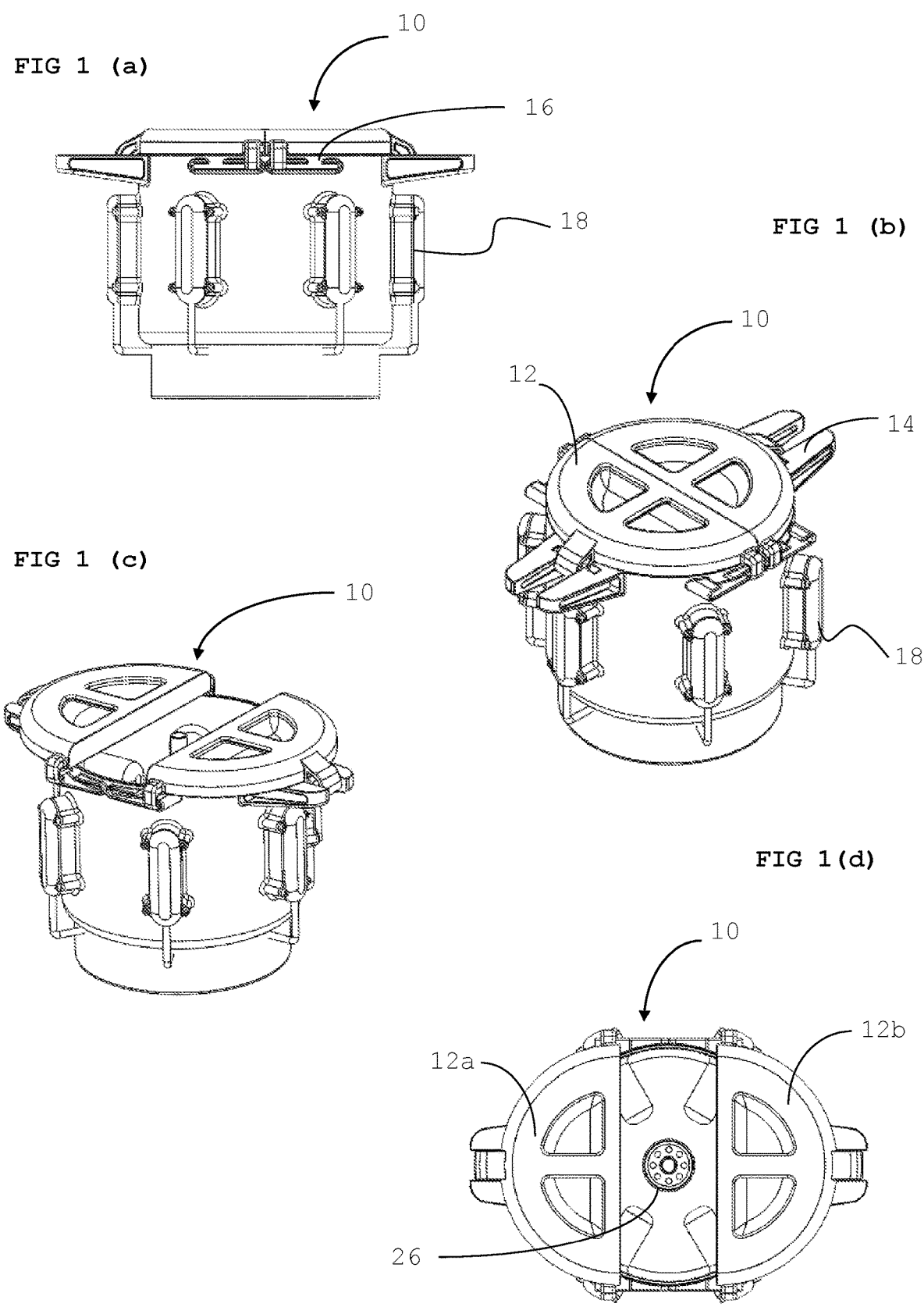

BLOOD ANALYSIS DEVICES, SYSTEMS AND METHODS

CROSS REFERENCE TO RELATED APPLICATIONS

The present application is a U.S. national stage application of PCT International Application No. PCT/AU2020/050465, filed May 12, 2020, and published as PCT Publication WO/2020/227765 on Nov. 19, 2020, which claims priority to Australian Application No. AU 2019901615, May 12, 2019. The disclosures of all the foregoing applications are hereby incorporated by reference in their entirety into the present application.

TECHNICAL FIELD

The present invention generally relates to blood analysis devices, and more particularly relates to systems and methods for analyzing blood properties.

BACKGROUND

A basic metabolic panel (BMP) is a blood test consisting of a set of, for example, seven or eight biochemical tests and is one of the most common laboratory tests ordered by health care providers. One version with seven tests is often referred to by medical professionals in the United States as the "CHEM-7", or "SMA-7" (Sequential Multiple Analysis-7). The seven parts of a CHEM-7 are tests for: sodium (Na+), potassium (K+), chloride (Cl−), bicarbonate (HCO3−) or CO2, blood urea nitrogen (BUN), creatinine and glucose.

Centrifuges are also used to separate components of blood for use in blood analysis. For example, hematocrit centrifuges are used to measure the volume percentage of red blood cells in whole blood.

Often blood is taken from a vein of a patient and sent to an outside laboratory for analysis. The existing procedures can take more time than is desirable in many cases.

Accordingly, it is desirable to provide fast and convenient blood analysis devices, systems and methods. In addition, it is desirable to offer a non-invasive option for blood analysis. Furthermore, other desirable features and characteristics of the present invention will become apparent from the subsequent detailed description of the invention and the appended claims, taken in conjunction with the accompanying drawings and the background of the invention.

SUMMARY

In one aspect, a blood analysis device is provided that comprises a housing for receiving a human or animal body part or a container of blood. The housing comprises at least one wave emitter for emitting an emitted wave to target blood and at least one wave sensor for sensing a response wave after the emitted wave has interacted with the target blood. The at least one wave sensor is configured to output at least one sense signal allowing a frequency spectrum of the response wave to be constructed.

The frequency spectrum can include a multitude of narrowband frequency response components, a broadband response or a hyperspectral response, for example.

In another aspect, a blood analysis system comprises a housing for receiving a human or animal body part or a container of blood. The housing comprises at least one magnetic resonance imaging (MRI) device for imaging target blood, and an analyzer configured to receive imaging from the MRI device and, based thereon, to determine at least one blood characteristic of the target blood.

The blood analysis device disclosed herein is able to perform blood examination without using a traditional method of centrifuge filtration and separation agents to isolate different elements of the patient's blood to achieve an analysis of their plasma. The blood analysis device is able to use imaging technologies, such as ultrasound, magnetic resonance imaging (MRI) and hyperspectral imaging to perform a remote sensing blood analysis of the patient's plasma, which eliminates the need to tamper with the donor's blood physically.

The blood analysis device is able to achieve higher analytical accuracy of the donor's blood because of its ability to examine the plasma in its natural state without using centrifuge filtration. In an ultrasound imaging embodiment, pressure waves are produced/emitted by at least one transducer/emitter, which interact with target blood, for example plasma thereof. Components of the target blood have a unique frequency signature which can be determined to analyze different targets of the blood plasma and blood cells.

Ultrasound pressure waves and other imaging technologies can also detect numerous abnormalities of the blood and blood cell structures. Critical blood information can be collected by using imaging technology and by assigning a frequency signature to different target blood components. In this way, highly time efficient blood analysis results are obtained.

In one embodiment, a combination of hyperspectral imaging and ultrasound imaging is used in the blood analysis.

In embodiments, the housing comprises a cuff for receiving a limb of a human or animal user.

In embodiments, the housing comprises a receptacle for receiving and holding the container. In embodiments, the housing includes a gel that forms the receptacle.

In embodiments, the emitted wave is an ultrasound wave. In embodiments, the ultrasound wave is a broadband or multispectral wave. In embodiments, broadband or multispectral ultrasound image detection is performed by the at least one wave sensor.

In embodiments, the emitted wave is an electromagnetic wave. In embodiments, the electromagnetic wave is a broadband or multispectral electromagnetic wave. In embodiments, broadband, multispectral or hyperspectral electromagnetic image detection is performed by the at least one wave sensor.

In embodiments, the at least one wave sensor comprises a hyperspectral image sensor.

In embodiments, the at least one wave emitter comprises a plurality of wave emitters and the at least one wave sensor comprises a plurality of wave sensors so that at least two pairs of wave emitters and wave sensors are oppositely arranged about the housing.

In embodiments, the at least one wave emitter comprises at least one ultrasound wave emitter and at least one electromagnetic wave emitter and the at least one wave sensor comprises at least one ultrasound sensor and at least one hyperspectral image sensor.

In embodiments, the at least one wave sensor is configured to output a spectral image of the target blood.

In another aspect, a blood analysis system is provided that includes a blood analysis device as described herein and at least one blood analyzer configured to receive the at least one sense signal and to perform a frequency spectrum analysis thereon and to determine at least one blood characteristic based on the frequency spectrum analysis.

In embodiments, the at least one blood characteristic comprises at least one of: HDL—High Density Lipoprotein Level, LDL—Low Density Lipoprotein Level, Ratio of HDL and LDL, CRP—C-Reactive Protein Level of inflammation with the body, CBC Complete Blood Count, TSH—Thyroid-stimulating hormone level, INR—International Normalized Ratio, LFT—Liver Function Test, U+E—Urea and Electrolytes, CMP—Comprehensive Metabolic Panel, WBC—White Blood Cell Count, RBC—Red Blood Cell Count, HBC—Hemoglobin Level of hemoglobin molecules, HCT—Hematocrit Level, PLT—Platelets level, sodium, potassium, chloride, bicarbonate, blood urea nitrogen (BUN), magnesium, creatinine, glucose, and/calcium, Blood Cell characteristics, Blood Cell Wall Thickness, Blood Cell Quality, Blood Cell Quantity, Blood Cell Age, Blood Cell Damage, Blood Minerals, Immune Cells, Cancer Cells, Viruses, Bacteria, Blood Pressure, triglyceride levels, carbon dioxide and/or oxygen levels and Blood Velocity.

In embodiments, the at least one blood analyzer comprises at least one computer processor and computer processor instructions for performing the frequency spectrum analysis.

In embodiments, the at least one blood analyzer is included in the housing, is provided remotely (e.g. cloud based) or a combination thereof.

In embodiments, the at least one blood analyzer is configured to compare spectral readings of the at least one sense signal with at least one reference frequency spectrum signature corresponding to the at least one blood characteristic.

In a further aspect, a blood analysis method comprises providing a blood analysis device. The device comprises a housing for receiving a human or animal body part or a container of blood. The housing comprises at least one wave emitter, and at least one wave sensor. The at least one emitter emits an emitted wave to target blood. The at least one wave sensor senses a response wave after the emitted wave has interacted with the target blood. The at least one wave sensor outputs at least one spectral sense signal. At least one blood analyzer receives the at least one spectral sense signal, performs a frequency spectrum analysis thereon and determines at least one blood characteristic based on the frequency spectrum analysis.

In embodiments, the housing comprises a cuff for receiving a limb of a human or animal user or wherein the housing comprises a receptacle for receiving and holding the container.

In embodiments, the at least one wave sensor comprises at least one of a hyperspectral image sensor and an ultrasound wave sensor.

In embodiments, the frequency spectrum analysis comprises comparing spectral components of the at least one spectral sense signal with at least one reference frequency spectrum signature corresponding to the at least one least one blood characteristic. For example, the frequency spectrum analysis comprises comparing normalized intensity values at different frequency points in the at least one spectral sense signal with reference values corresponding to the at least one reference frequency spectrum signature.

In another aspect, a blood analysis method comprises providing a blood analysis device. The device comprises a housing for receiving a human or animal body part or a container of blood. The housing comprises an imaging device for imaging, e.g., MRI imaging, target blood. At least one blood analyzer receives imaging from the imaging device and performs an imaging analysis thereon and determines at least one blood characteristic based on the imaging analysis.

In yet a further aspect, a blood analysis device is provided that comprises at least one wave emitter for emitting an emitted wave to target blood and at least one wave sensor for sensing a response wave after the emitted wave has interacted with the target blood. The at least one wave sensor is configured to output at least one sense signal allowing a frequency spectrum of the response wave to be constructed.

In a further aspect, a blood analysis method comprises providing a blood analysis device. The device comprises a housing for receiving a human or animal body part or a container of blood. The housing comprises at least one wave emitter, and at least one wave sensor. The at least one emitter emits an emitted wave to target blood. The at least one wave sensor senses a response wave after the emitted wave has interacted with the target blood. The at least one wave sensor outputs at least one spectral sense signal. At least one blood analyzer receives the at least one spectral sense signal, performs a frequency spectrum analysis thereon and determines at least one blood characteristic based on the frequency spectrum analysis.

In another aspect there is disclosed a blood analysis system comprises at least one wave emitter for emitting an emitted wave to target blood; at least one wave sensor for sensing a response wave after the emitted wave has interacted with the target blood, the at least one wave sensor configured to output at least one sense signal allowing a frequency spectrum of the response wave to be constructed, and at least one blood analyzer configured to receive the at least one sense signal and to perform a frequency spectrum analysis thereon and to determine at least one blood characteristic based on the frequency spectrum analysis.

In a further aspect there is disclosed a blood analysis method, comprising the steps of: providing at least one wave emitter and at least one wave sensor; the at least one wave emitter emitting an emitted wave to target blood; the at least one wave sensor sensing a response wave after the emitted wave has interacted with the target blood, wherein the at least one wave sensor outputs at least one spectral sense signal; at least one blood analyzer receiving the at least one spectral sense signal, and performing a frequency spectrum analysis on the at least one spectral sense signal and determining at least one blood characteristic based on the frequency spectrum analysis.

Preferably the method includes the step of providing a blood analysis device having a housing operatively associated with the at least one wave emitter, the housing adapted to receive (i) a human or animal body part, or (ii) a container of blood.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Figure 1:
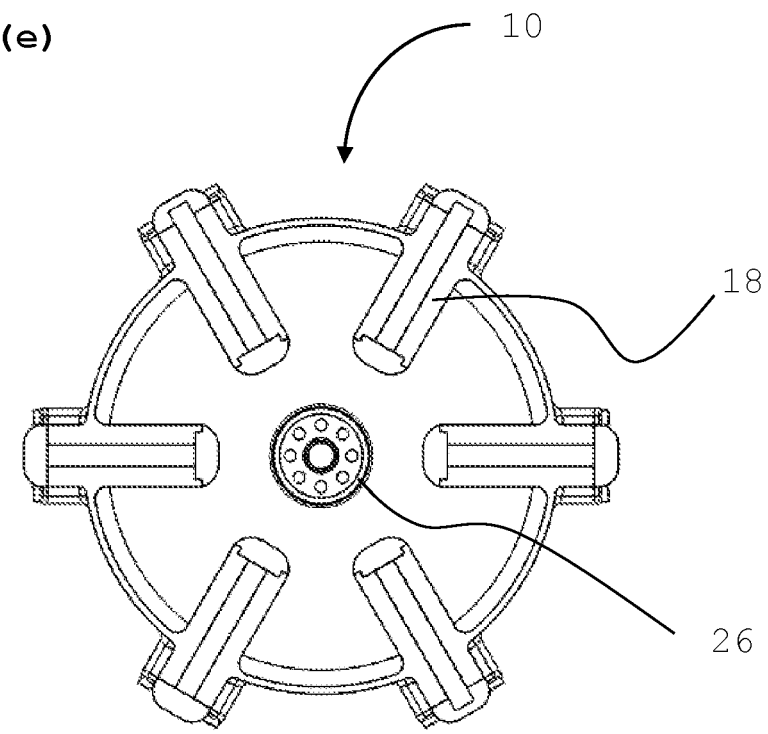
FIGS. 1(a) to 1(g) are various views of a first blood analysis device, in accordance with various embodiments.
Figure 1:
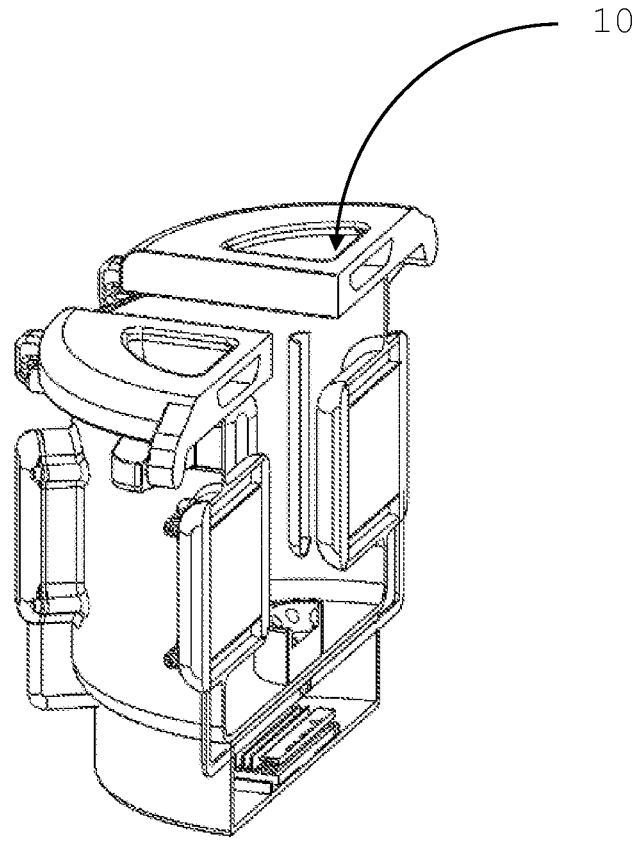
Figure 1:
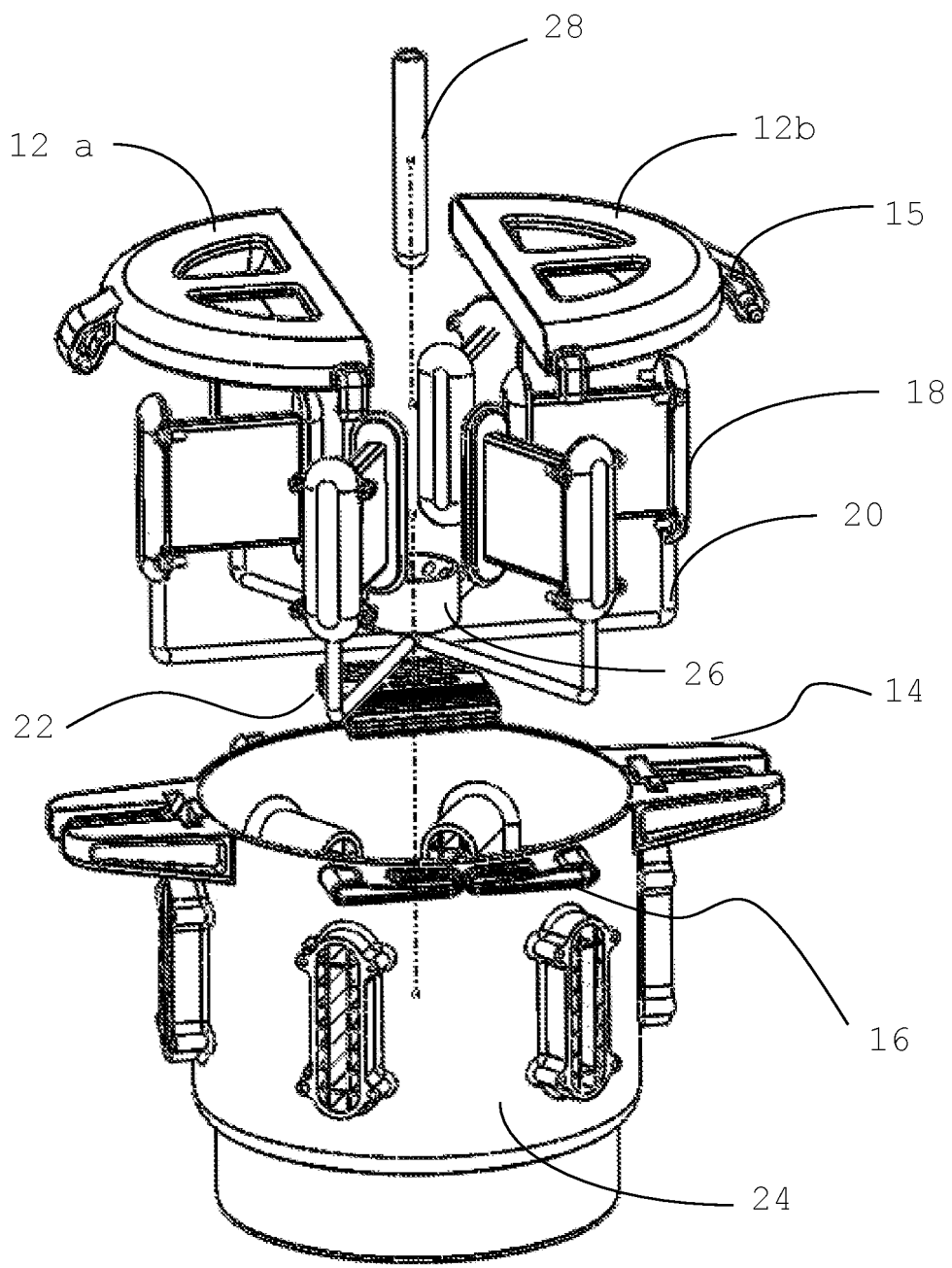
Figure 2:
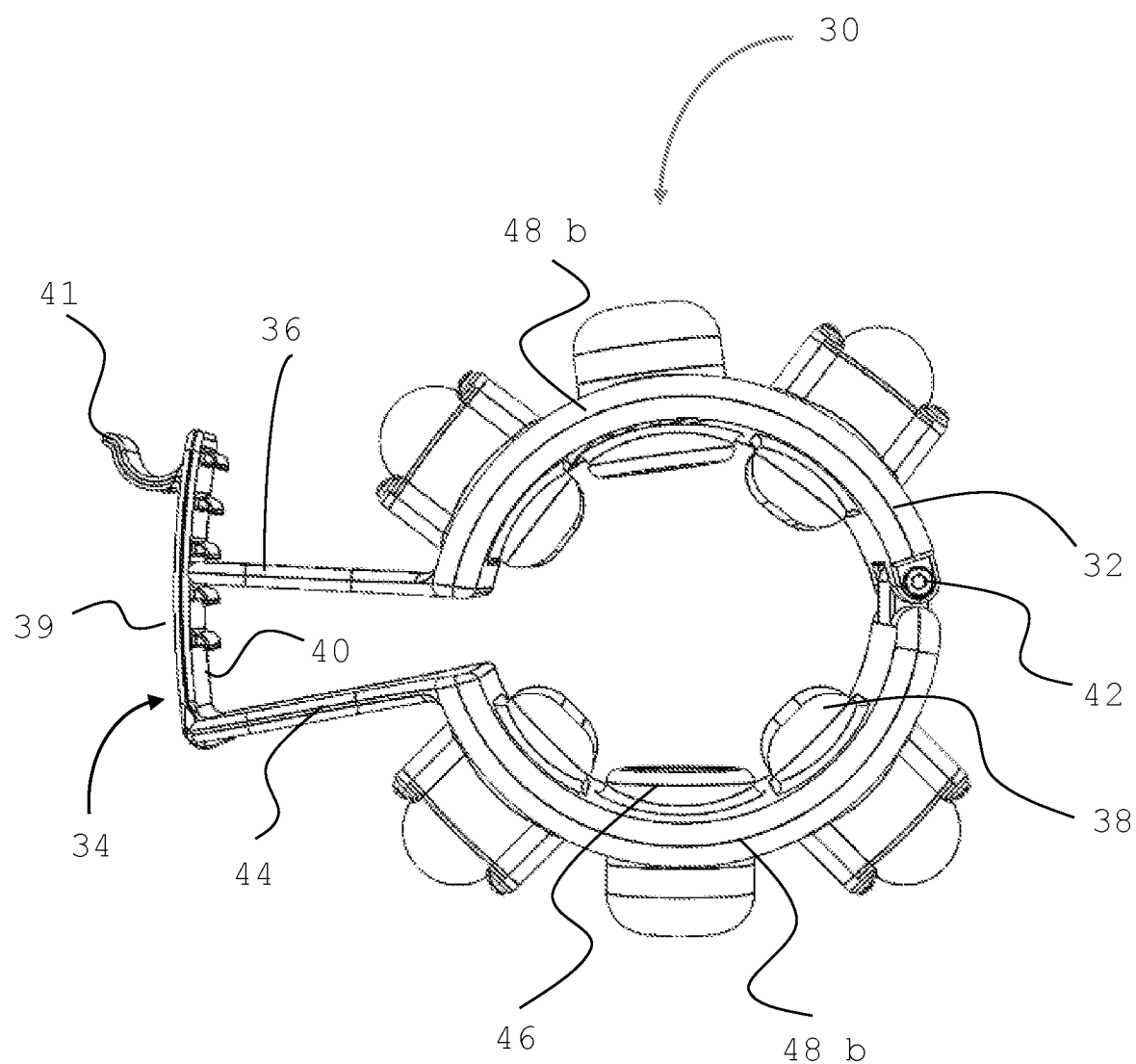
FIGS. 2(a) to 2(d) are various views of a second blood analysis device, in accordance with various embodiment.
Figure 2:
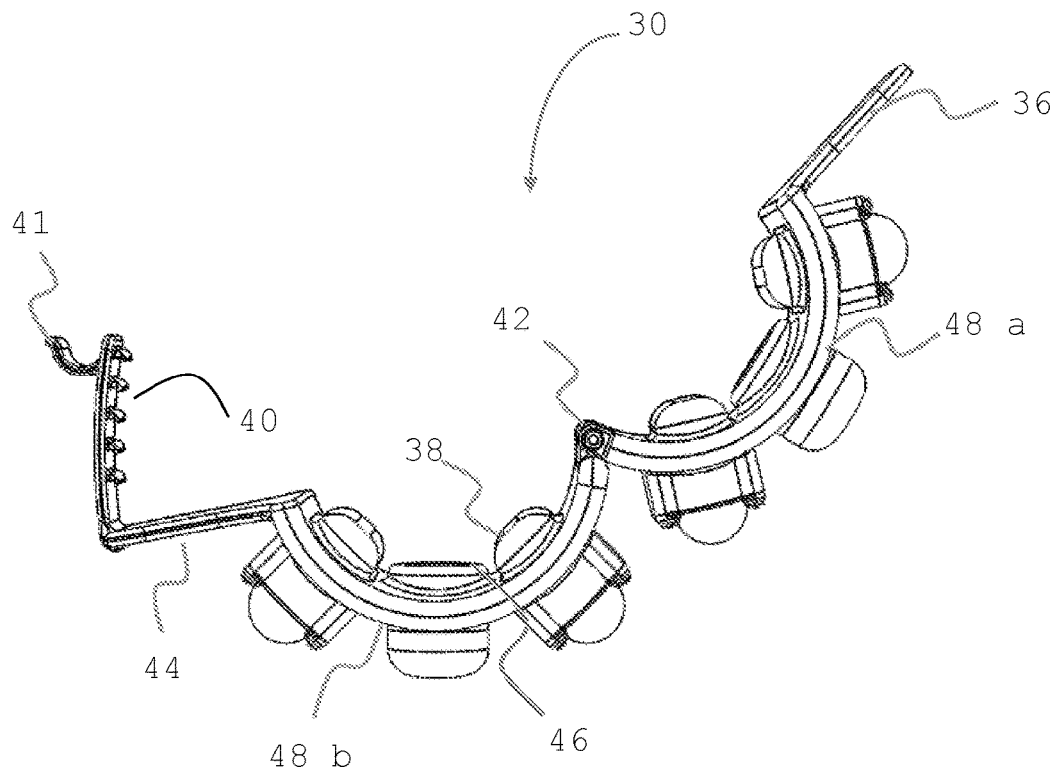
Figure 2:
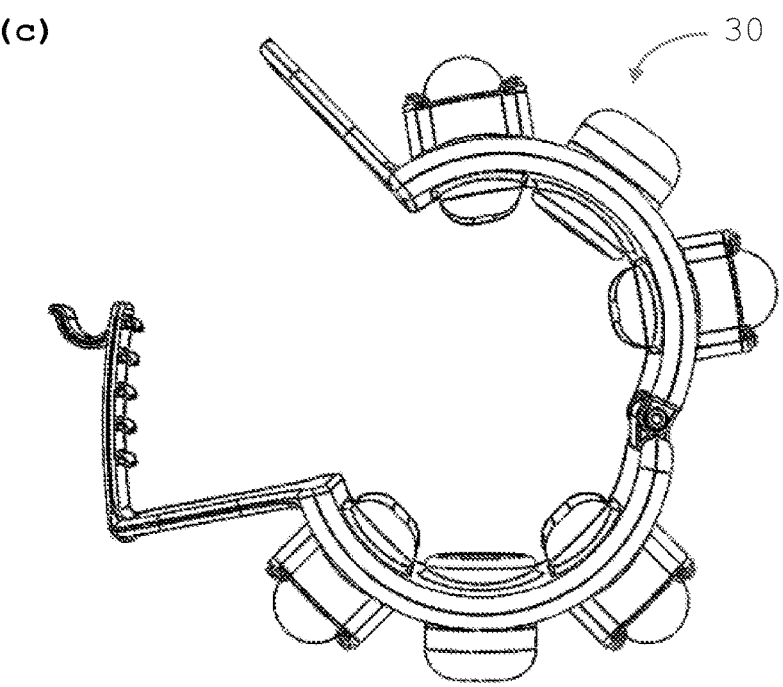
Figure 2:
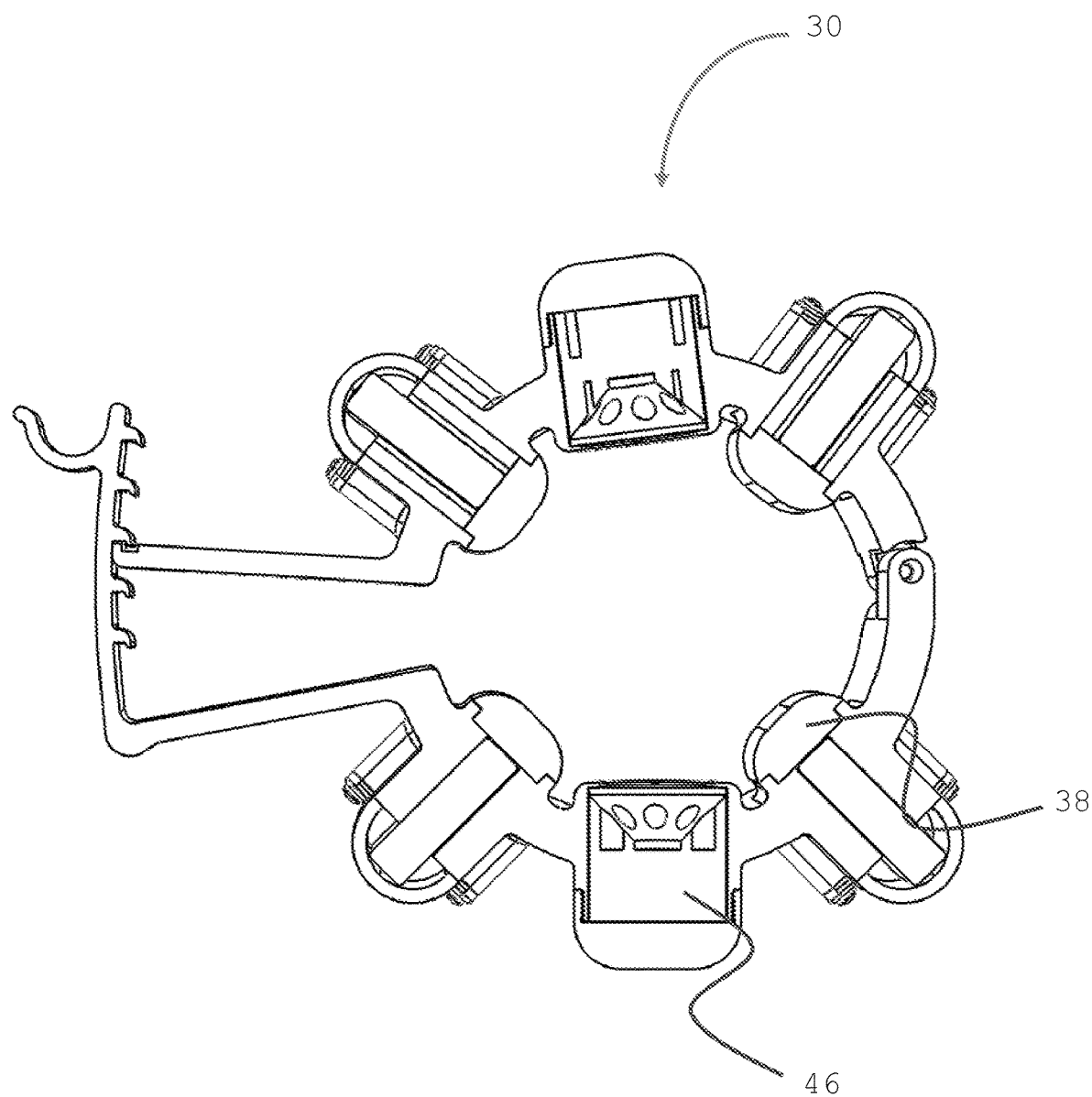

With reference to FIGS. 1 and 2, the present disclosure provides a blood analysis device 10, 30 that includes one or more imaging/sensing devices 18, 26 for imaging blood contained in a vial 28 or other container or in-vivo blood. In an embodiment according to FIG. 1, the blood analysis device 10 is operable to stand on a table or other surface and receive a vial 28 of blood for imaging. In another embodiment according to FIG. 2, the blood analysis device 30 forms a cuff and is operable to be wrapped around a limb, e.g., an arm of a patient, to image blood in-vivo. In these embodiments, blood is imaged, and the images are analyzed by an internal and/or external processing unit 22 including an image analyzer to determine blood characteristics. In embodiments, ultrasound, MRI and/or hyperspectral imaging is utilized. Imaging herein is used in a broad sense to refer to one or more sensing elements (e.g. a grid of pixels) for detecting ultrasound, electromagnetic or other waves and determining an intensity or other measurement thereof. Sensed measurements can be collected and compared with reference values forming a signature representing blood characteristics. Thus, the imaging can provide one or more measurement signatures for comparison with reference signatures.

Turning to FIGS. 1(a) to 1(g), an embodiment of a first blood analysis device 10 is shown. The blood analysis device 10 includes a housing 24, which is in a bucket shape in the exemplary embodiment. The housing 24 has a bottom configured for standing on a horizontal surface such as a table or a desk. The housing 24 includes a plurality of imaging/sensing devices 18. In particular, the imaging/sensing devices 18 include ultrasound transducers/emitters and ultrasound sensors. In the exemplary embodiment, three pairs of oppositely disposed imaging/sensing devices 18 are included. However, less or more imaging/sensing devices 18 could be included. The imaging/sensing devices 18 are circumferentially distributed about, and fixed to, the housing 24. The housing 24 further includes a different type of imaging/sensing device 26, which is a hyperspectral imaging device in the exemplary embodiment. By providing a combination of different types of imaging/sensing devices 18, 26, greater information on the target blood is available for subsequent analysis and blood characterization. Although a combination of ultrasound and hyperspectral imaging/sensing devices 18, 26 are disclosed in the present embodiment, other imaging/sensing medians are envisaged that allow blood properties to be determined such as miniature MRI devices and the like. In one embodiment, an inner space defined by the housing 24 is filled with solid silicone gel to reduce ultrasonic pressure wave impedance.

In embodiments, the hyperspectral imaging/sensing device 26 includes multiple LED lights to assist hyperspectral imaging. The hyperspectral electromagnetic waves are captured by a hyperspectral camera for subsequent analysis. In embodiments, the processing unit 22 is configured to activate one ultrasound imaging/sensing device (transducer/emitter 18) to emit an ultrasound pressure wave and to sense the emitted wave using a plurality of the other ultrasound imaging/sensing devices (sensors 18) after the emitted wave has interacted with target blood in the vial 28. In this way, loss of ultrasound imaging information is minimized.

In the embodiment of FIGS. 1(a) to 1(g), the imaging/sensing devices 18, 26 are arranged on a frame 20 that supports the imaging devices and also allows imaging/sense data to be communicated there within to the processing unit 22. In some embodiments, the processing unit 22 is configured to receive and externally transmit captured imaging/sense data for external analysis. In other embodiments, the processing unit 22 is configured to analyze the captured imaging/sense data to determine blood characteristics. In embodiments, the processing unit 22 includes a microprocessor or other computer processor device and memory storing instructions thereon for controlling operation of the imaging/sensing devices 18, 26. In particular, the processing unit 22 is configured to activate the imaging/sensing devices 18, 26, to capture imaging/sense data and either to transmit the captured (and optionally pre-processed) imaging/sense data for blood analysis processing at an external blood analyzer or to analyze the imaging/sense data onboard to determine blood characteristics. In embodiments, blood analysis of the imaging/sense data includes comparing the images/sense data with a database of blood image/sense signatures to determining blood characteristics. In embodiments where ultrasound and/hyperspectral imaging/sensing is utilized, spectral components of the imaging/sense data are compared with spectral imaging/sense data stored in a reference database to characterize the blood.

The blood analysis device 10 of the exemplary embodiment of FIGS. 1(a) to 1(g) includes a cover 12 that allows the housing 24 to be closed during activation of the imaging/sensing devices 18, 26. In the illustrated exemplary embodiment, first and second covers 12a, 12b open and close by sliding atop housing 24. The specific mechanism shown is a sliding cooperation of brackets 14, 15 of the housing 24 and the cover 12 and a sliding cooperation of projection and guide 16, 17 between the housing 24 and the cover 12. Other cooperative structures for allowing the cover first and second covers 12a, 12b to slide away and towards one another when opening and closing are envisaged. Further, alternative opening and closing structures can be provided such as hinges to allow for a vertical opening and closing. In the exemplary embodiment of FIG. 1, the cover 12 opens and closes by manual operation. However, an electrified (e.g. motor operated) cover 12 is possible.

The blood analysis device 10 could include a (rechargeable) battery for supplying the imaging/sensing devices 18, 26 with power. Alternatively, a power cord socket could be included for the supply of electrical power.

With reference to FIGS. 2(a) to 2(d), an embodiment of a second blood analysis device 30 is illustrated. The blood analysis device 30 includes a housing 32 in the shape of a cuff for wrapping around a limb of a subject, such as the upper arm. The housing 32 includes first and second housing parts 48a, 48b that are connected at a hinge 42 to allow the housing 32 to open to receive the upper arm and to close about the upper arm. The housing 32 includes a latch 34 to hold the housing 32 in the closed configuration. The latch 34 includes a first arm 36 and a second arm 44 connected at the ends of respective housing parts 48a, 48b. The second arm 44 includes a plate 39 connected thereto and the plate 39 has a plurality of ribs 40 respectively defining differing degrees of closure of the housing 32 when engaged by the first arm 36. A release tab 41 is included on an outside of the plate 39 to facilitate release of the latch 34 to open the housing 32. Thus, the latch 34 has different latch positions (provided in one embodiment by ribs 40) so that the housing 32 can accommodate different size upper arms.

In embodiments, the housing 32 holds a plurality of imaging/sense devices 38, 46. In some embodiments, different types of imaging/sense devices 38, 46 are included in housing 32. In one exemplary embodiment, one or more ultrasound devices 38 are included and one or more hyperspectral imaging/sense devices 46 are included. MRI imaging and other suitable imaging/sense medians could be used. The imaging/sense devices 38, 46 are directed toward the inside of the cuff shaped housing to image/sense blood flowing within veins of a subject.

Although not shown in FIGS. 2(*a*) to 2(*d*), a processing unit is included in the housing 32 for controlling activation of the imaging/sense devices 38, 46 and for controlling capture of imaging/sense data. The processing unit is configured to process the imaging/sense data to determine blood characteristics or to transmit the captured imaging/sense data (optionally after pre-processing) to an external processor for analysis to determine blood characteristics. Further, the blood analysis device 30 includes a battery (e.g. a rechargeable battery) for supplying power to the imaging/sense devices 38, 46 and the processing unit.

Figure 3A:
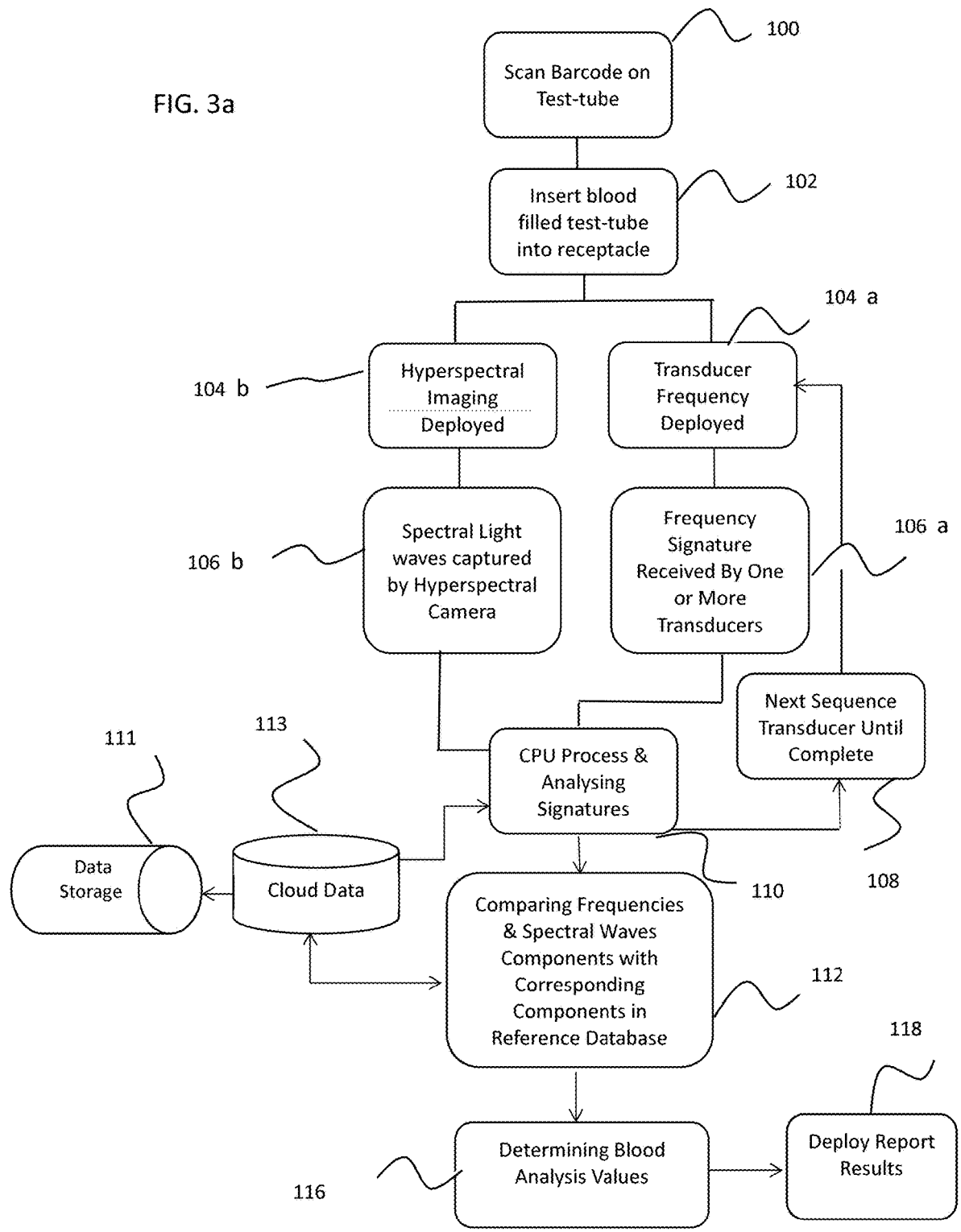
FIG. 3(a) is a flow chart of a method of blood analysis, in accordance with various embodiments.
Figure 3B:
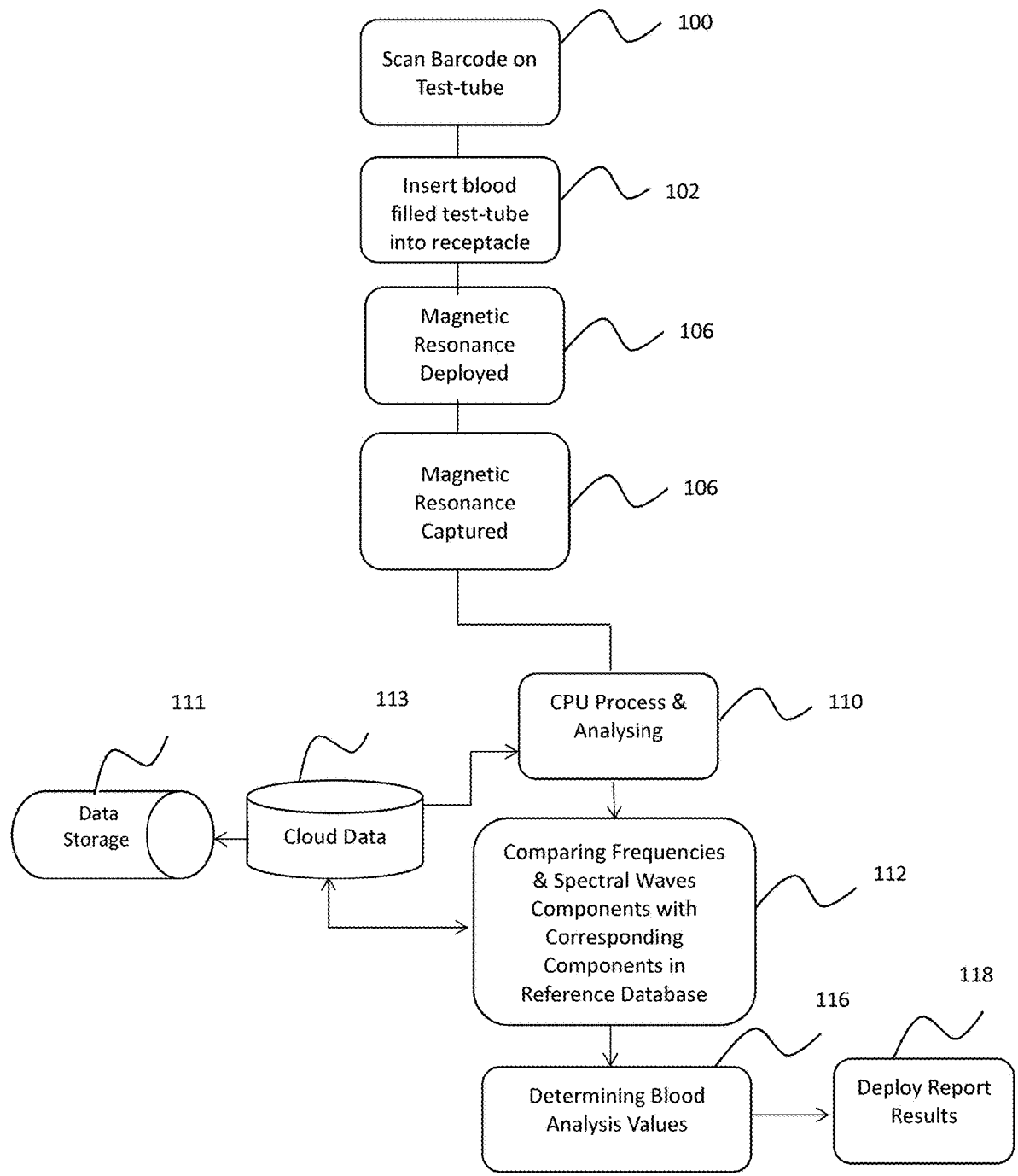
FIG. 3(b) is a flow chart of another method of blood analysis, in accordance with various embodiments.

FIG. 3 is a flow chart of one exemplary operation of the blood analysis devices 10, 30 described herein.

Steps 100 and 102 are concerned with the blood analysis device 10 of FIG. 1. In step 100, a bar code on the vial or test tube 28 is scanned by a bar code scanner (not shown), which can be internal to the blood analysis device 10 or a peripheral device. Other ways of uniquely identifying vial 28 are envisaged such as QR codes, and alphanumeric serial codes. In step 102, the vial 28 containing target blood is inserted into a receptacle defined by silicone gel included within the housing 24. Thus, the cover 12 is slid horizontally open with respect to the housing 24. For the blood analysis device 30 of FIG. 2, steps 100 and 102 are replaced with placing the housing 32 about the arm or leg of a subject and engaging the latch 34 at a latch position corresponding to a snug fit of the housing 32 to the subject body part. The remaining steps of the flow chart of FIG. 3 are common to both blood analysis devices 10, 30.

Step 104 includes activating the imaging/sensing devices 18, 26, 38, 46. In some embodiments, activating the imaging/sensing devices 18, 26, 38, 46 includes emitting ultrasonic waves from one or more ultrasonic imaging/sensing devices 18, 38 in sub-step 104 *a*. Additionally or alternatively, activating the imaging/sensing devices 18, 26, 38, 46 includes emitting electromagnetic radiation from one or more hyperspectral imaging devices 26, 46 in sub-step 104*b*. In step 106 imaging/sense data of target blood is captured with a sensor 18, 26, 38, 46. In some embodiments, capturing imaging/sense data step 106*b* includes capturing hyperspectral data that has interacted with blood using hyperspectral imaging camera/sensor 26, 46. Additionally or alternatively, ultrasonic pressure waves that have interacted with target blood are detected using ultrasonic sensor/camera 18, 38 in step 106*b*. In step 108, plural imaging/sensing devices 18, 26, 38, 46 are sequentially activated and imaging data is captured from one or more image sensing devices 18, 26, 38, 46.

In step 110, the imaging data that has been captured in foregoing steps is processed. In one embodiment, step 110 includes transmitting the captured image/sense data to an external processor or performing processing using processing unit 22. Transmission of imaging/sense data can use Wi-Fi, Bluetooth, Zigbee or any other data transmission scheme. Processing is performed on the captured image/sense data. In one example, spectrally focused (e.g. narrowband focused) imaging/sense data is identified that corresponds to known signatures for blood characteristics. One or more spectral filters may be used to spectrally focus the captured imaging data. In embodiments processing step 110 results in multiple spectrally focused imaging/sense data components corresponding to known signatures of blood characteristics. For example, step 110 includes providing normalized intensity values at different frequency points in the measured data for comparison in step 112 (described below) with reference values corresponding to a signature for a particular blood characteristic.

In step 112, spectrally focused imaging data is compared to reference signature data obtained from reference database 111 (which may be updated from the cloud 113 periodically). That is, reference image/sense signatures including data points at a plurality of specific frequencies (e.g. narrowband signatures) are compared to imaging/sense data from step 110 having data points at corresponding specific frequencies to determine matching data that is indicative of blood characteristics. In this way, blood characteristics as described herein are determined in step 116.

In step 118, the blood analysis results from step 116 are stored and reported. In one example, a cloud-based results database is accessed to retrieve the blood analysis, for example, using a unique code associated with the patient or the vial 28 (e.g. as obtained from the bar code). In embodiments, the blood analysis report is printed on physical medium or displayed on a screen.

FIG. 3(*b*) illustrates another exemplary embodiment of blood analysis using an MRI method. MRI data capture could be used additionally or alternatively to the ultrasound or hyperspectral sensing methods described above with respect to FIG. 3(*a*). The method is largely the same as that described with respect to FIG. 3(*a*). As such, the process will not be further described expect with regard to steps 104', 106' 110' and 112'. In these steps, MRI data capture (step 106') is used on target blood in a vial or in a limb of a patient. Different aspects (e.g. measurements at different frequency combinations) of the MRI data are grouped into measurement signatures for comparison with reference signatures in steps 110' and 112' to determine values for respective blood characteristics. Thus, blood analysis values are determined in step 116' and reported in step 118'.

In a non-illustrated embodiment there is disclosed a blood analysis device for use in a doctor's waiting room and adapted to perform diagnostics on patients in the waiting room. The blood analysis device may for example be placed on a reception desk or mounted to a wall. The blood analysis device includes at least one wave emitter for emitting an emitted wave to a patient (target blood) and at least one wave sensor, here a hyperspectral image sensor for sensing a response wave after the emitted wave has interacted with the patient in the waiting room. The at least one wave sensor is configured to output at least one sense signal allowing a frequency spectrum of the response wave to be constructed. In this embodiment, blood of a patient is imaged, and the images are analyzed by a processing unit including an image analyzer to determine blood characteristics. In this embodiment, hyperspectral imaging is utilized to detect waves and determine an intensity or other measurement thereof. Such sensed measurements are collected and compared with reference values forming a signature representing blood characteristics. Thus, the imaging can provide one or more measurement signatures for comparison with reference signatures, making it possible to detect diseases while a patient is waiting in the waiting room. It will be appreciated that use of the blood analysis device need not be limited to doctors' waiting rooms but could be employed in public spaces and be employed for detecting diseases in animals.

While at least one exemplary aspect has been presented in the foregoing detailed description of the invention, it should be appreciated that a vast number of variations exist. It should also be appreciated that the exemplary aspect or exemplary aspects are only examples, and are not intended to limit the scope, applicability, or configuration of the invention in any way. Rather, the foregoing detailed description will provide those skilled in the art with a convenient road map for implementing an exemplary aspect of the invention. It being understood that various changes may be made in the function and arrangement of elements described in an exemplary aspect without departing from the scope of the invention as set forth in the appended claims.

The invention claimed is:

1. A blood analysis device, comprising:
a housing operatively associated with a plurality of imaging and sensing devices configured respectively with at least one wave emitter and at least one wave sensor;
wherein the housing is adapted to:
a cuff operable to be wrapped around a limb of a human or animal body part, or a bucket shaped receptacle for receiving and holding a container of blood;
the at least one wave emitter emitting an emitted wave to target blood in the container or the limb of the human or animal body part,
the at least one wave sensor sensing a response wave after the emitted wave has interacted with the target blood, the at least one wave sensor configured to output at least one sense signal allowing a frequency spectrum of the response wave to be constructed;
and a processing unit including a frequency spectrum analyzer configured to determine blood characteristics data and compare with a reference value to determine blood characteristics for external analysis, wherein the processing unit is configured to receive and externally transmit the blood characteristic data wirelessly, and
the cuff comprising:
a first and a second housing parts that are connected at a hinge to allow the housing to open to receive the limb of the human or animal body part and to close the limb;
a latch to hold the housing in the closed configuration, the latch including a first arm and a second arm connected at the ends of the first and a second housing parts respectively;
the second arm including a plate which has a plurality of ribs defining differing degrees of closure of the housing when engaged by the first arm; and
a release tab included on an outside of the plate to facilitate release of the latch to oven the housing.

2. The blood analysis device of claim 1, wherein the receptacle is filled with solid silicone gel to reduce ultrasonic pressure wave impedance.

3. The blood analysis device of claim 1, wherein the emitted wave is an ultrasound wave.

4. The blood analysis device of claim 3, wherein the ultrasound wave is a broadband or multispectral wave.

5. The blood analysis device of claim 1, wherein the emitted wave is an electromagnetic wave.

6. The blood analysis device of claim 5, wherein the electromagnetic wave is a broadband or multispectral electromagnetic wave.

7. The blood analysis device of claim 1, wherein the at least one wave sensor comprises a hyperspectral image sensor.

8. The blood analysis device of claim 1, wherein the at least one wave emitter comprises a plurality of wave emitters and the at least one wave sensor comprises a plurality of wave sensors so that at least two pairs of wave emitters and wave sensors are oppositely arranged about the housing.

9. The blood analysis device of claim 1, wherein the at least one wave emitter comprises at least one ultrasound wave emitter and at least one electromagnetic wave emitter and the at least one wave sensor comprises at least one ultrasound sensor and at least one hyperspectral image sensor.

10. The blood analysis device of claim 1, wherein the at least one wave sensor is configured to output a spectral image of the target blood.

11. A blood analysis system comprising:
a blood analysis device according to claim 1 having at least one blood analyzer including at least one computer processor and computer processor instructions for performing the frequency spectrum analysis; and
the at least one blood analyzer configured to receive the at least one sense signal and to perform a frequency spectrum analysis thereon and to determine at least one blood characteristic based on the frequency spectrum analysis;
wherein the at least one blood analyzer is configured to compare spectral readings of the at least one sense signal with at least one reference frequency spectrum signature corresponding to the at least blood characteristic;
wherein the computer processor is configured to receive and externally transmit the spectral readings of the at least one sense signal wirelessly; and
wherein the spectral readings of the at least one sense signal is compared with a reference signature data obtained from a reference database updated periodically from a cloud.

12. The blood analysis system of claim 11, wherein the at least one blood characteristic comprises at least one of:
HDL—High Density Lipoprotein Level;
LDL—Low Density Lipoprotein Level;
Ratio of HDL and LDL;
CRP—C-Reactive Protein Level of inflammation with the body;
CBC—Complete Blood Count;
TSH—Thyroid-stimulating hormone level;
INR—International Normalized Ratio;
LFT—Liver Function Test;
U+E—Urea and Electrolytes;
CMP—Comprehensive Metabolic Panel;
WBC—White Blood Cell Count;
RBC—Red Blood Cell Count;
HBC—Hemoglobin Level of hemoglobin molecules;
HCT—Hematocrit Level;
PLT—Platelets Level;
sodium, potassium, chloride, bicarbonate, blood urea nitrogen (BUN), magnesium, creatinine, glucose, and/calcium;
Blood Cell characteristics;
Blood Cell Wall Thickness;
Blood Cell Quality;
Blood Cell Quantity;
Blood Cell Age;
Blood Cell Damage;
Blood Minerals;
Immune Cells;
Cancer Cells;
Viruses;
Bacteria;
Blood Pressure;
triglyceride levels;
carbon dioxide and/or oxygen levels; and
Blood Velocity.

13. The blood analysis system of claim 11, wherein the at least one blood analyzer is included in the housing, remotely or a combination thereof.

* * * * *